United States Patent
Weiss et al.

(10) Patent No.: US 11,298,343 B2
(45) Date of Patent: Apr. 12, 2022

(54) METHOD FOR TREATING THALASSEMIA

(71) Applicant: ST. JUDE CHILDREN'S RESEARCH HOSPITAL, Memphis, TN (US)

(72) Inventors: Mitchell J. Weiss, Memphis, TN (US); Mondira Kundu, Memphis, TN (US); Christophe Lechauve, Bartlett, TN (US)

(73) Assignee: ST. JUDE CHILDREN'S RESEARCH HOSPITAL, Memphis, TN (US)

(*) Notice: Subject to any disclaimer, the term of this patent is extended or adjusted under 35 U.S.C. 154(b) by 68 days.

(21) Appl. No.: 16/758,986

(22) PCT Filed: Oct. 26, 2018

(86) PCT No.: PCT/US2018/057709
§ 371 (c)(1),
(2) Date: Apr. 24, 2020

(87) PCT Pub. No.: WO2019/084402
PCT Pub. Date: May 2, 2019

(65) Prior Publication Data
US 2020/0345702 A1 Nov. 5, 2020

Related U.S. Application Data

(60) Provisional application No. 62/578,104, filed on Oct. 27, 2017.

(51) Int. Cl.
| | | |
|---|---|---|
| *A61K 31/7052* | (2006.01) | |
| *A61K 31/495* | (2006.01) | |
| *A61K 31/4164* | (2006.01) | |
| *A61P 7/06* | (2006.01) | |
| *A61K 31/436* | (2006.01) | |
| *A61K 45/06* | (2006.01) | |

(52) U.S. Cl.
CPC .............. *A61K 31/436* (2013.01); *A61P 7/06* (2018.01); *A61K 45/06* (2013.01)

(58) Field of Classification Search
CPC .............. A61K 31/7052; A61K 31/495; A61K 31/4164; A61P 7/06
USPC ..................... 514/43, 252.12, 399
See application file for complete search history.

(56) References Cited

U.S. PATENT DOCUMENTS

2006/0154950 A1   7/2006   Bianchi
2008/0075692 A1   3/2008   Perrine

OTHER PUBLICATIONS

Ganley, I.G., D.H. Lam, J. Wang, X. Ding, S. Chen & X. Jiang (2009) "ULK1-ATG13-FIP200 Complex Mediates mTOR Signaling and Is Essential for Autophagy," Journal of Biological Chemistry 284:12297-12305.
Honda, S., S. Arakawa, Y. Nishida, H. Yamaguchi, E. Ishii & S. Shimizu (2014) "Ulk1-mediated Atg5-independent macroautophagy mediates elimination of mitochondria from embryonic reticulocytes," Nature Communications 5:4004.
Hosokawa, N., T. Hara, T. Kaizuka, C. Kishi, A. Takamura, Y. Miura, S-i. Iemura, T. Natsume, K. Takehana, N. Yamada, J.-L. Guan, N. Oshiro & N. Mizushima (2009) "Nutrient-dependent mTORCI Association with the ULK1-Atg13-FIP200 Complex Required for Autophagy," Molecular Biology of the Cell 20:1981-1991.
International Preliminary Report on Patentability in PCT/US2018/057709 dated May 7, 2020.
International Search Report and Written Opinion in PCT/US2018/057709 dated Jan. 7, 2019.
Khandros, E., C.S. Thom, J. D'Souza & M.J. Weiss (2012) "Integrated protein quality-control pathways regulate free α-globin in murine β-thalassemia," Blood 119(22):5265-5275.
Kim, J., M. Kundu, B. Viollet & K-L Guan (2011) "AMPK and mTOR regulate autophagy through direct phosphorylation of Ulk1," Nature Cell Biology 13(2):132-141.
Kitagawa, K., Y. Kotake, Y Hiramatsu, N. Liu, S. Suzuki, S. Nakamura, A Kikuchi & M. Kitagawa (2010) "GSK3 regulates the expressions of human and mouse c-Myb via different mechanisms," Cell Division 5:27.
Kundu, M., T. Lindsten, C.-Y. Yang, J. Wu, F. Zhao, J. Zhang, M.A. Salek, P.A. Ney & C.B. Thompson (2008) "Ulk1 plays a critical role in the autophagic clearance of mitochondria and ribosomes during reticulocyte maturation," Blood 112(4): 1493-1502.
Laplante, M. & D.M. Sabatini (2012) "mTOR Signaling in Growth Control and Disease," Cell 149:274-293.
Mishida, Y., S. Arakawa, K. Fujitani, H. Yamaguchi, T. Mizuta, T. Kanaseki, M. Komatsu, K. Otsu, Y. Tsujimoto & S. Shimizu (2009) "Discovery of Atg5/Atg7-independent Alternative Macroautophagy," Nature 461(7264):654-8.
Zhang, X, G. Camprecios, P. Rimmele, R. Liang, S. Yalcin, S.K. Mungamuri, J. Barminko, V. D'Escamard, M.H. Baron, C. Brugnara, D. Papatsenko, S. Rivella & S. Ghaffari (2014) "FOXO3-mTOR Metabolic Cooperation in the Regulation of Erythroid Cell Maturation and Homeostasis," American Journal of Hematology 89(10):954-963.

*Primary Examiner* — Raymond J Henley, III
(74) *Attorney, Agent, or Firm* — Licata & Tyrrell P.C.

(57) ABSTRACT

Methods for removing excess free α-globin in erythroid cells and treating a thalassemia using an agent that activates Unc-51 Like autophagy activating Kinase (ULK) are described.

7 Claims, 1 Drawing Sheet

METHOD FOR TREATING THALASSEMIA

This application is a U.S. National Stage Application of PCT/US2018/057709 filed Oct. 26, 2018 and claims the benefit of priority of U.S. Provisional Application No. 62/578,104, filed Oct. 27, 2017, the contents of each of which are incorporated herein by reference in their entirety.

INTRODUCTION

This invention was made with government support under Grant Numbers DK061692 and HL114697 awarded by the National Institutes of Health. The government has certain rights in the invention.

BACKGROUND

The production of functional hemoglobin A (HbA) tetramers ($\alpha_2\beta_2$) requires the coordinated synthesis and assembly of $\alpha$- and $\beta$-globin protein chains and iron-containing heme groups. Individually, all HbA components are toxic to red blood cells. In particular, $\beta$-thalassemias are common hemoglobinopathies in which $\beta$-globin gene (HBB) mutations cause the buildup of free $\alpha$-globin. These unpaired $\alpha$ chains initiate an oxidative damage cascade and form damaging precipitates that contribute largely to the clinical problems associated with $\beta$-thalassemia.

The pathophysiology of $\beta$-thalassemia bears similarities to a diverse group of protein-aggregation diseases affecting multiple organs. These disorders, which include Parkinson disease, Alzheimer disease, Huntington disease, amyotrophic lateral sclerosis, and $\alpha_1$-antitrypsin deficiency, are caused by the accumulation of unstable, relatively insoluble proteins. It is believed that the affected cells can detoxify and remove these damaging proteins via multiple interacting biochemical pathways called protein quality-control (PQC) pathways, but that disease ensues when such compensatory mechanisms are overwhelmed. Cellular PQC systems include molecular chaperones, ubiquitin-mediated proteolysis, and autophagy. Several lines of evidence suggest that $\beta$-thalassemic erythroid cells use PQC pathways to detoxify free $\alpha$-globin. Specifically, the clinical severity of $\beta$-thalassemia is proportional to the degree of $\alpha$-globin excess; there is a threshold below which excess $\alpha$-globin is less harmful, as illustrated by subjects with the $\beta$-thalassemia trait, who experience 50% reduced $\alpha$-globin synthesis with minimal clinical manifestations or accumulation of $\alpha$-globin precipitates; and there is direct biochemical evidence that $\alpha$-globin interacts with cellular PQC components.

Studies have shown that normal and $\beta$-thalassemic erythroid precursors can balance globin ratios through selective $\alpha$-chain proteolysis. Pulse-chase experiments using intact human $\beta$-thalassemic erythroid cells and cell lysates showed that excessive a chains are actively degraded and accumulate mainly in the late stages of erythroid maturation, presumably as the proteolytic capacity becomes exceeded. The ubiquitin proteasome system (UPS) is responsible for physiologic degradation of native proteins and for removing misfolded proteins as part of the PQC pathway in all cells. Studies have shown that normal and $\beta$-thalassemic hemolysates can ubiquitinate and degrade exogenous $\alpha$-globin although the associated pathways remain largely uncharacterized. Red blood cell (RBC) precursors also use autophagy, a group of related processes in which targeted proteins or organelles are delivered to lysosomes and degraded. For example, autophagy-related genes are up-regulated by the master erythroid transcription factor GATA-1 during terminal erythropoiesis. During reticulocyte maturation, mitochondria are eliminated by "macroautophagy" or "mitophagy," a process in which cells form double-membrane vesicles (autophagosomes) around cytoplasmic contents for delivery to lysosomes. Notably, electron micrographs of $\beta$-thalassemic erythroblasts identify a subset of $\alpha$-globin precipitates within lysosomes. More recent work indicates that autophagic processes are increased in HbE/$\beta$-thalassemia. In particular, it has been shown that interregulated PQC pathways, including the ubiquitin proteasome system (UPS), autophagy, and heat-shock protein responses, are used to detoxify and remove free $\alpha$-globin in $\beta$-thalassemic erythroid cells and that the UPS is regulated dynamically at the transcriptional level in $\beta$-thalassemic erythroblasts through a Nrf1 stress-response pathway (Khandros, et al. (2012) *Blood* 119(22):5265-5275).

Autophagy is promoted by AMP-activated protein Kinase (AMPK), which is a key energy sensor and regulates cellular metabolism to maintain energy homeostasis. Conversely, autophagy is inhibited by the Mechanistic Target Of Rapamycin (mTOR), a central cell-growth regulator that integrates growth factor and nutrient signals. In vivo inhibition of mTOR remarkably improves erythroid cell maturation and anemia in a model of 3-thalassemia (Zhang, et al. (2014) *Am. J. Hematol.* 89(10):954-963).

Unc-51 Like autophagy activating Kinase 1 (ULK1) has been suggested to be a molecular mechanism underlying how AMPK regulates autophagy. Under glucose starvation, AMPK promotes autophagy by directly activating ULK1 through phosphorylation of Ser317, Ser555 and Ser777. Under nutrient sufficiency, high mTOR activity prevents ULK1 activation by phosphorylating ULK1 Ser757 and disrupting the interaction between ULK1 and AMPK. See Kim, et al. (2011) *Nature Cell Biol.* 13:132-141. Using knockout mouse models, it has been further shown that ULK1 is a component of the autophagy machinery that leads to the elimination of organelles in erythroid cells via a non-canonical pathway that does not require certain core components of the autophagy machinery, such as Atg5 and Atg7 (Kundu, et al. (2008) *Blood* 112:1493-1502; Honda, et al. (2014) *Nat. Commun.* 5:4004; Nashida, et al. (2009) *Nature* 461(7264):654-8).

SUMMARY OF THE INVENTION

The present invention provides methods for removing excess free $\alpha$-globin in erythroid cells and treating a thalassemia using an effective amount of an agent that activates Unc-51 Like autophagy activating Kinase (ULK). In one embodiment, the agent agonizes UNK1/2, AMP-Activated Protein Kinase (AMPK) or Glycogen synthase kinase 3 (GSK3). In another embodiment, the agent inhibits Mechanistic Target Of Rapamycin (mTOR). In certain embodiments, the thalassemia is $\beta$-thalassemia.

DETAILED DESCRIPTION OF THE INVENTION

Figure 1:
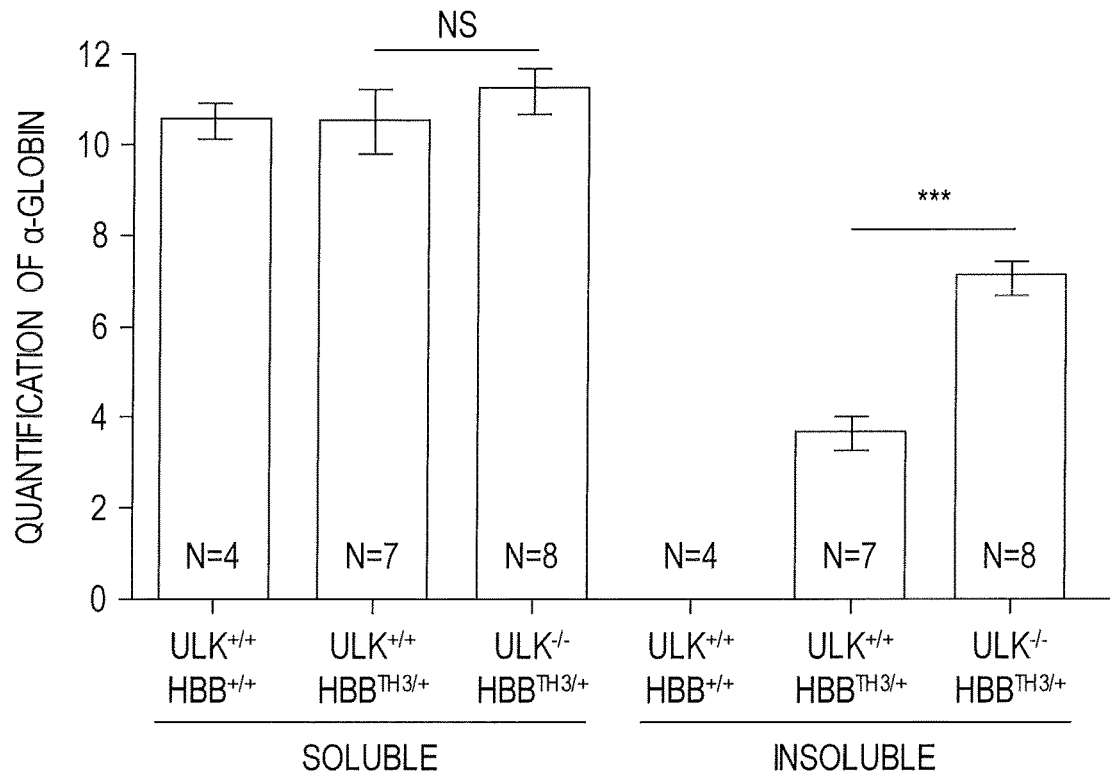
FIG. 1 shows quantification of soluble and insoluble $\alpha$-globin chains in circulating erythrocytes from wild-type (Ulk1$^{+/+}$Hbb$^{+/+}$), Ulk1$^{+/+}$Hbb$^{Th3/+}$ and Ulk1$^{-/-}$Hbb$^{Th3/+}$ mice. Hbb$^{+/+}$Ulk1$^{+/+}$, n=4; Hbb$^{Th3/+}$Ulk1$^{+/+}$, n=8; Hbb$^{Th3/+}$Ulk1$^{-/-}$, n=8. Results are presented as mean±SD; ***P<0.0001; n.s., not significant.

The accumulation of free α-globin is a major determinant of the pathophysiology of β-thalassemia. Using a mouse model for β-thalassemia, it has now been shown that the ULK1 gene, which encodes a protein that drives some forms of autophagy, participates in removal of excess free α-globin. Specifically, genetic ablation of ULK1 in β-thalassemia mice results in increased accumulation of free α-globin and exacerbation of the anemia phenotypes. By comparison, systemic treatment with rapamycin to inhibit the ULK1 inhibitor mTORC1 reduces α-globin precipitates and lessens pathologies in β-thalassemic mice, but not in those lacking ULK1. Similarly, rapamycin reduces free α-globin accumulation in erythroblasts derived from β-thalassemic patient CD34$^+$ hematopoietic progenitors. Accordingly, the present invention provides compositions and methods for removing excess free α-globin and treating a thalassemia disorder through the induction, activation or agonism of endogenous ULK1/2 in erythrocytes. In particular, the methods of the invention include the administration of an effective amount of one or more agents that induce, activate or agonize endogenous ULK1/2 to treat, delay or prevent the adverse effects of a thalassemia disorder.

The term "thalassamia" or "thalassamia disorder" refers to a group of inherited autosomal recessive blood disorders that are common in various areas of the world including Mediterranean regions, India and Southeast Asia. In thalassemia, the genetic defect, which could be either a point mutation or deletion, results in a reduced rate of synthesis or no synthesis of one of the globin chains that make up hemoglobin. This can cause toxic buildup of the unaffected chain and also inhibit the production of normal hemoglobin, both causing anemia, the characteristic presenting symptom of the thalassemias. The two major forms of the disorder are alpha- and beta-thalassamia. "Beta-thalassamia" or "β-thalassemia" is a common inherited hemoglobinopathy characterized by impaired or absent β-globin gene production with consequent accumulation of unpaired α-subunits. The excess of unbound free α-globins precipitate in maturing erythroid cells and induces the production of reactive oxygen species (ROS) resulting in cellular oxidative stress damage and death of erythroid precursors, a process termed ineffective erythropoiesis. The presence of α-globin precipitates is also associated with a reduced RBC half-life and the clinical features of β-thalassemia, highlighting the importance of α-globin precipitates in the pathogenesis of the disease. By comparison "alpha-thalassemia" or "α-thalassemia" is a form of thalassemia involving the genes HBA1 and HBA2. Alpha-thalassemia is due to impaired production of 1, 2, 3 or 4 α-globin chains, leading to a relative excess of β-globin chains. The degree of impairment is based on which clinical phenotype is present (how many chains are affected). In certain embodiments, the subject treated in accordance with the methods described herein has β-thalassamia.

The subject treated in accordance with the methods described herein can be any mammal, including, but not limited to, humans, murines, simians, felines, canines, equines, bovines, mammalian farm animals, mammalian sport animals, and mammalian pets. Ideally, the subject is a human subject. In certain embodiments, the methods described herein are used to treat β-thalassemia in a subject, such as transfusion-dependent β-thalassemia (i.e., "Cooley's anemia"), non-transfusion-dependent β-thalassemia, β-thalassemia major, β-thalassemia intermedia, β-thalassemia minor, or β-thalassemia with associated hemoglobin (Hb) abnormalities (e.g., HbC/β-thalassemia, HbE/β-thalassemia, HbS/β-thalassemia). Thalassemia major is characterized by reduced Hb level (<7 g/dl), mean corpuscolar volume (MCV)>50<70 fl and mean corpuscolar Hb (MCH)>12<20 pg and requirements for regular red blood cell transfusions every 3-4 weeks. Thalassemia intermedia is characterized by Hb level between 7 and 10 g/dl, MCV between 50 and 80 fl and MCH between 16 and 24 pg and intermittent RBC transfusion requirements. Thalassemia minor is characterized by reduced MCV and MCH, with increased HbA2 level.

"Treatment," as used herein, refers to the application or administration of an agent, or pharmaceutical composition containing the agent, to a subject, isolated tissue, isolated cells or cell line from a subject, where the subject has a thalassemia disorder, or a predisposition toward development of a thalassemia disorder, where the purpose is to cure, heal, alleviate, relieve, alter, remedy, ameliorate, improve, or affect the thalassemia disorder and/or any associated symptoms of the thalassemia disorder, or the predisposition toward the development of the thalassemia disorder. Ideally, treatment of a subject, tissue or cell will reduce anemia, ineffective erythropoiesis and/or transfusion burden in a subject with β-thalassemia.

An "effective amount" is an amount sufficient to effect beneficial or desired results. An effective amount can be administered in one or more administrations. An effective amount corresponds with the quantity required to provide a desired average local concentration of a particular biologic agent, in accordance with its known efficacy, for the intended period of therapy. A dose may be determined by those skilled in the art by conducting preliminary animal studies and generating a dose response curve, as is known in the art. Maximum concentration in the dose response curve would be determined by the solubility of the agent in the solution and by toxicity to the animal model, as known in the art.

In some embodiments, treatment of a subject with an agent of the invention removes excess free α-globin in erythroid cells by at least 20% as compared to free α-globin levels in the subject within 1, 2, 3, or 4 weeks prior to the commencement of treatment of the subject. In certain embodiments, treatment removes excess free α-globin in erythroid cells of the subject by at least 50%. In certain embodiments, excess free α-globin is reduced in erythroid cells of the subject by at least 25%, 30%, 33%, 35%, 40%, 45%, 50%, 55%, 60%, 65%, 70%, 75%, 80%, 85%, 90%, 95%, 98%, or 100%. A reduction in free α-globin levels can be measured by its predicted downstream effects including increased RBC number, improved RBC morphology, reduced reticulocyte count and reduced ineffective erythropoiesis. In addition, a reduction in free α-globin levels determined by measuring α-globin levels before and after treatment using routine methods including, but not limited to cellulose acetate electrophoresis and DE-52 microchromatography, TRITON acetic acid (TAU) urea gel electrophoresis and electron microscopy, high-performance liquid chromatography (HPLC), ELISA, western blot analysis, dot blot analysis and the like.

Subjects with thalassemia typically exhibit RBC morphologic changes (microcytosis, hypochromia, anisocytosis, poikilocytosis (spiculated tear-drop and elongated cells)), and nucleated RBC (i.e., erythroblasts). Accordingly, in certain embodiments, treatment of a subject according to the methods provided herein improves red blood cell morphology in the subject as compared to the red blood cell morphology in the subject within 1, 2, 3, or 4 weeks prior to the commencement of treatment of the subject according to the methods provided herein. Non-limiting determinants of improved red blood cell morphology include a 5% to 100% reduction in the ratio of number of abnormal red blood cells in the subject to the total number of red blood cells in the subject, a 5% to 100% reduction in the ratio of the number of red blood cells with basophilic stippling in the subject to the total number of red blood cells in the subject, a 5% to 100% reduction in the ratio of the number of poikilocytic red blood cells in the subject to the total number of red blood cells in the subject, a 5% to 100% reduction in the ratio of the number of schistocytes in the subject to the total number of red blood cells in the subject, and a 5% to 100% reduction in the ratio of the number of irregularly contracted red blood cells in the subject to the total number of red blood cells in the subject within 1, 2, 3, or 4 weeks prior to the commencement of treatment of the subject.

Agents of use in the method of this invention include agents that activate the expression or activity of ULK1 and/or ULK2. Such agents include agonists that directly interact with ULK1/2 protein or nucleic acids, as well as agents that indirectly activate ULK1/2 expression or activity. Agents that directly agonize ULK1/2 include, e.g., U-11 (1-(2-((4-chlorophenyl)methoxy)-2-(2,4-dichloro phenyl) ethyl)-1H-imidazol) and derivatives thereof having the structure of Formula I, II or III:

Formula I
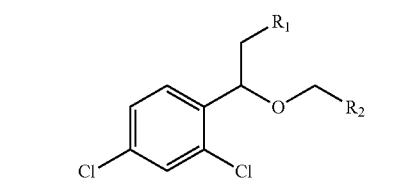

Formula II
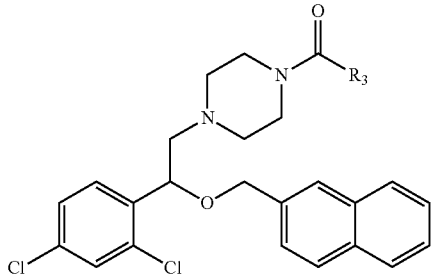

Formula III
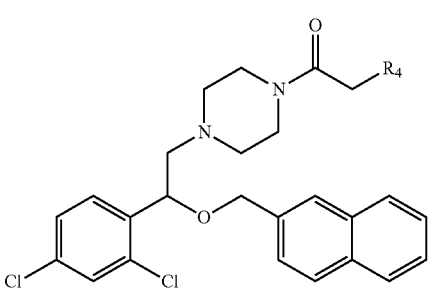

wherein $R_1$ is N-Boc-piperazinyl, benzimidazolyl, imidazolyl or triazolyl; $R_2$ is p-bromophenyl, p-chlorophenyl, 2-naphthyl; $R_3$ is phenyl, p-methoxylphenyl, p-methylphenyl, o-chlorophenyl, 2,4-dichlorobenzenyl, p-bromophenyl, p-nitrophenyl, 4-pyridenyl, p-methylbenzyl, p-methoxybenzyl, p-chlorobenzyl, p-bromobenzyl; and $R_4$ is di-n-butylamine, diisobutylamine, pyrrole, piperidine, N-methylpiperazine, N-ethylpiperazine or morpholine. See Zhang, et al. (2017) Chem. Sci. 8:2687-2701 and CN 106478550. Additional agents that directly agonize ULK1/2 include compounds having the structure of Formula IV:

Formula VI
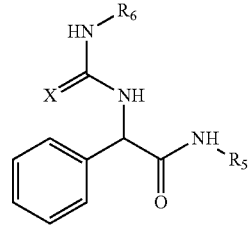

wherein X is O or S; $R_5$ is:

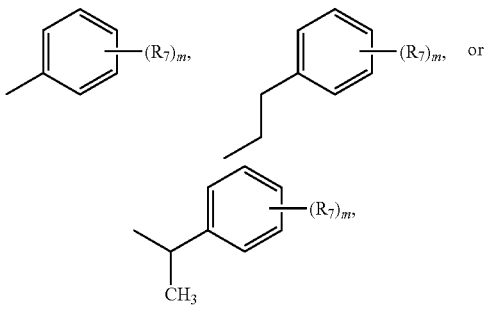

wherein $R_7$ hydrogen, alkyl, alkoxy or halogen; and m is 1 or 2; and $R_6$ is:

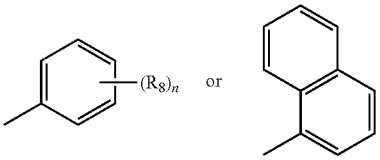

wherein $R_8$ hydrogen, alkyl, alkoxy, haloalkyl or halogen; and n is 1 or 2. See CN 106748892. In certain embodiments, the ULK1 agonist is LYN-1604 (CAS No. 2088939-99-3).

Agents of use in the methods of this invention that indirectly activate ULK1/2 expression or activity include molecules that agonize AMPK or GSK3 and/or molecules that antagonize mTOR.

AMPK is a highly conserved serine/threonine protein kinase that regulates cellular metabolism, proliferation, and aging processes. In response to decreases in intracellular ATP, AMPK is activated and serves as a metabolic checkpoint, restoring ATP levels through acute regulation of metabolic enzymes and inhibition of pro-growth anabolic pathways. In mammals, phosphorylation of ULK1 by AMPK is required for ULK1 function in the response to nutrient deprivation. AMPK directly activates ULK by phosphorylation (Egan, et al. (2011) *Science* 331(6016):456-461). In addition, AMPK suppresses mTOR activity and mTOR inhibits ULK1. Through this multi-prong approach, AMPK controls ULK1 thereby ensuring activation only under the appropriate cellular conditions (Egan, et al. (2011) *Science* 331(6016):456-461; Kim, et al. (2011) *Nat. Cell Biol.* 13(2):132-141).

AMPK agonists are known in the art and include, but are not limited to, 5-aminoimidazole-4-carboxamide riboside (AICA riboside or AICAR); AICAR monophosphate (ZMP); guanidine; galegine; metformin (dimethylbiguanide); phemformin (phenethylbiguanide); antifolate drugs that inhibit AICAR transformylase (e.g., methotrexate, pemetrexed); thiazolidinediones (e.g., rosiglitazone, pioglitazone, or troglitazone); 2-Deoxyglucose (2-DG); phenobarbital; A-769662 (CAS No. 844499-71-4); PT1 (CAS No. 331002-70-1); and salicylate. See, e.g., Hardie, et al. (2012) *Chem. Biol.* 19:1222-1236; Hawley, et al. (2012) *Science* 336:918-922. A number of other small molecule inhibitors of AMPK are known in the art, including C24 (Li, et al. (2013) *Toxicol. Appl. Pharmacol.* 273(2):325-34); A-769662 (4-hydroxy-3-[4-(2-hydroxyphenyl)phenyl]-6-oxo-7H-thieno[2,3-b]pyridine-5-carbonitrile; Cool, et al. (2006) *Cell Metab.* 3(6):403-16); D942 (5-[3-[4-[2-(4-fluorophenyl) ethoxy]phenyl]propyl] furan-2-carboxylic acid); ZLN024 (Zhang, et al. (2013) *PLoS ONE* 8(8):e72092), salinomycin (Zhu, et al. (2013) *PLoS ONE* 8(12):e84175). In addition, AMPK agonists are described in U.S. Pat. Nos. 8,604,202; 8,592,594; 8,586,747; 8,563,746; 8,546,427; 8,563,729; 8,394,969; 8,329,914; 8,329,738; US 2012/0172333; US 2011/0060001; US 2009/0105293; EP 2519527; WO 2010/073011; and WO 2013/003467.

Glycogen synthase kinase-3 (GSK3) is a highly conserved and ubiquitously expressed serine/threonine kinase that phosphorylates proteins containing clustered serine or threonine residues that are separated by four amino acids. Although GSK3 was originally identified as a kinase that phosphorylates glycogen synthase, subsequent studies have demonstrated that it has broader range of substrates including β-catenin, tau, myelin basic protein, cyclin D1, GATA4, c-jun, c-myc, CREB, initiation factor eIF2B, heat shock factor-1, and p53. Through the phosphorylation of this diverse set of substrates, GSK3 regulates embryonic development and proliferative responses in adult tissues, and is implicated in several human disease states including tumorigenesis, Alzheimer's disease, and diabetes. In addition, signaling from GSK3 to TIP60 and ULK1 has been shown to regulate autophagy when deprived of serum but not glucose (Lin, et al. (2012) *Science* 336:477-81).

GSK3 agonists are known in the art and include, but are not limited to, Differentiation-inducing factor (DIF)-1 [1-(3,5-dichloro-2,6-dihydroxy-4-methoxyphenyl)-1-hexanone] and DIF-3, the monochlorinated analog of DIF-1; sodium nitroprusside (Mariappan, et al. (2014) *J. Biol. Chem.* 289:35363-35375); Ly-294,002 (CAS 154447-36-6, Albrecht, et al. (2015) *J. Cell Biol.* 208:597-612); wortmannin (Zhang, et al. (2015) *PLoS ONE* 10:30131525); and 6-hydroxydopamine (Hernandez-Baltazar, et al. (2013) *PLoS ONE* 8(8):e70951).

Mammalian Target Of Rapamycin (mTOR), also known as FK506-binding protein 12-rapamycin-associated protein 1 (FRAP1), is a core component of two distinct protein complexes, mTOR complex 1 and mTOR complex 2, which regulate different cellular processes. In particular, mTOR regulates cell growth, cell proliferation, cell motility, cell survival, protein synthesis, autophagy, and transcription (Lipton & Sahin (2014). *Neuron.* 84(2):275-291; Hay & Sonenberg (2004) *Genes Dev.* 18(16):1926-45). mTOR also functions to promote the activation of insulin receptors and insulin-like growth factor 1 receptors (Yin, et al. (2016) *Cell Res.* 26:46-65) and phosphorylates Atg13, ULK1 and ULK2 (Jung, et al. (2009) *Mol. Biol. Cell* 20:1992-2003; Kim, et al. (2011) *Nat. Cell Biol.* 13:132-141) to inhibit their activities.

As used herein, an mTOR inhibitor includes, but is not limited to, rapamycin (also known as sirolimus) and rapalogs thereof including everolimus (40-O-2-hydroxyethyl-rapamycin or RAD001), zotarolimus (40-epi-tetrazolyl-rapamycin or ABT-578), 32-deoxorapamycin (SAR-943), 16-pent-2-ynyloxy-32-deoxorapamycin, 16-pent-2-ynyloxy-32 (S or R)-dihydro-rapamycin, 16-pent-2-ynyloxy-32 (S or R)-dihydro-40-O-2-hydroxyethyl-rapamycin, temsirolimus (40-[3-hydroxy-2-hydroxymethyl-2-methylpropanoate]-rapamycin or CCI-779), deforolimus (ridaforolimus, MK-8669 or AP-23573), pimecrolimus, tacrolimus (FK-506), dactolisib (NVP-BE235 or BEZ235), BGT226 (NVP-BGT226, CAS No. 915020-55-2), SF1126 (CAS No. 936487-67-1), Gadatolisib (PKI-587 or PF-05212384), sapanisertib (INK 128), AZD8055 (CAS No. 1009298-09-2), AZD2014 (CAS No. 1009298-59-2), 40-O-dimethylphosphinyl-rapamycin, 40-O-2-ethoxyethyl-rapamycin, CC-115 (CAS No. 1228013-15-7), CC-223 (CAS No. 1228013-30-6), PI-103 (CAS No. 371935-74-9), Ku-0063794 (CAS No. 938440-64-3), PF-04691502 (CAS No. 1013101-36-4), CH5132799 (CAS No. 1007207-67-1), GDC-0980 (RG7422, CAS No. 1032754-93-0), Torin 1 (CAS No. 1222998-36-8), WAY-600 (CAS No. 1062159-35-6), WYE-125132 (WYE-132, CAS No. 1144068-46-1), WYE-687 (CAS No. 1062161-90-3), Omipalisib (GSK-2126458), PP-121 (CAS No. 1092788-83-4), OSI-027 (CAS No. 936890-98-1), Palomid 529 (CAS No. 914913-88-5), torkinib (PP242, CAS No. 1092351-67-1), voxtalisib (XL765 or SAR245409, CAS No. 1349796-36-6), GSK1059615 (CAS No. 958852-01-2), and WYE-354 (CAS No. 1062169-56-5). See also, WO 1998/002441, WO 2001/014387, WO 2004/101583, WO 1992/005179, WO 1994/002136, WO 1994/002385 and WO 1996/013273.

In some embodiments, the mTOR inhibitor is an ATP-competitive mTOR kinase inhibitor (e.g., rapamycin or rapamycin analogs). In other embodiments, the mTOR inhibitor is an mTOR/PI3K dual inhibitor (e.g., dactolisib, BGT226, SF1126 or Gadatolisib). In further embodiments, the mTOR inhibitor is an mTORC1/mTORC2 dual inhibitor (e.g., sapanisertib, AZD8055 or AZD2014). In particular embodiments, the mTOR inhibitor is an mTOR/PI3K dual inhibitor or an mTORC1/mTORC2 dual inhibitor and not an ATP-competitive mTOR kinase inhibitor.

Ideally, the agents of the present invention are formulated together with a pharmaceutically acceptable carrier and provided as a pharmaceutical composition. Pharmaceutical formulations comprising the of the invention may be prepared for storage by mixing the agent having the desired degree of purity with optional physiologically acceptable carriers, excipients or stabilizers (Remington: The Science and Practice of Pharmacy 20$^{th}$ edition (2000)), in the form of aqueous solutions, lyophilized or other dried formulations. Therefore, the invention further relates to a lyophilized or liquid formulation containing an agent that activates ULK1/2. As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, oral, topical, transdermal, intranasal, spinal or epidermal administration (e.g., by injection or infusion). Depending on the route of administration, the agent may be coated in a material to protect the agent from the action of acids and other natural conditions that may inactivate the agent.

The agents of the invention may include one or more pharmaceutically acceptable salts. A "pharmaceutically acceptable salt" refers to a salt that retains the desired biological activity of the parent compound and does not impart any undesired toxicological effects (see, e.g., Berge, et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic hydroiodic phosphorous and the like as well as from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N-dibenzylethylenediamine, N-methylglucamine, chloroprocaine, choline, diethanolamine, ethylenediamine, procaine and the like.

A pharmaceutical composition of the invention also may include a pharmaceutically acceptable antioxidant. Examples of pharmaceutically acceptable antioxidants include water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydro xyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of an injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition. Prolonged absorption of the injectable compositions can be brought about by including in the composition an agent that delays absorption for example, monostearate salts and gelatin.

Sterile injectable solutions can be prepared by incorporating the active compound in the required amount in an appropriate solvent with one or a combination of ingredients enumerated above, as required, followed by sterilization micro filtration. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation are vacuum drying and freeze-drying (lyophilization) that yield a powder of the active ingredient plus any additional desired ingredient from a previously sterile-filtered solution thereof.

The amount of agent that can be combined with a carrier material to produce a single dosage form will vary depending upon agent, the subject being treated, and the particular mode of administration. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. In accordance with this invention, daily doses of may be in the range of about 0.01 mg to 100 mg, or about 0.1 to 50 mg. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. For example, when administering rapamycin, a dose in the range of about 0.1 mg to 20 mg per day, or more preferably about 0.05 mg to 5 mg per day, or most preferably about 0.5 mg to 2 mg per day may be given. Similarly, when administering everolimus (a rapalog), a dose in the range of about 0.5 mg to 30 mg per day, or more preferably about 1 mg to 20 mg per day, or most preferably about 2.5 mg to 10 mg per day may be given.

Alternatively, the agents of the invention can be administered as a sustained release formulation in which case less frequent administration is required. Dosage and frequency vary depending on the half-life of the compounds in the patient.

Actual dosage levels of the active compounds in the pharmaceutical compositions of the present invention may be varied so as to obtain an amount of the active compounds which is effective to achieve the desired therapeutic response for a particular patient, composition, and mode of administration, without being toxic to the patient. The selected dosage level will depend upon a variety of pharmacokinetic factors including the activity of the particular agent of the present invention employed, the route of administration, the time of administration, the rate of excretion of the particular agent being employed, the duration of the treatment, other drugs, compounds and/or materials used in combination with the particular compositions employed, the age, sex, weight, condition, general health and prior medical history of the patient being treated, and like factors well known in the medical arts.

A pharmaceutical composition of the present invention can be administered by one or more routes of administration using one or more of a variety of methods known in the art. As will be appreciated by the skilled artisan, the route and/or mode of administration will vary depending upon the desired results. Routes of administration for the agents according to the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, the agents of the invention can be administered by a nonparenteral route, such as a topical, epidermal or mucosal route of administration, for example, intranasally, orally, vaginally, rectally, sublingually or topically.

The following non-limiting examples are provided to further illustrate the present invention.

Example 1: Material and Methods

Mice. The breeding and analysis of Hbb$^{Th3+/-}$ and Ulk1$^{-/-}$ mice have been described previously (Khandros, et al. (2012) *Blood* 119:5265-5275; Kundu, et al. (2008) *Blood* 112:1493-1502; Ciavatta, et al. (1995) *Proc. Natl. Acad. Sci. USA* 92:9259-9263). EpoR-Cre mice, with Cre recombinase expressed from the endogenous erythropoietin receptor locus, were provided by Ursula Klingmüller (German Cancer Research Center, Heidelberg, Germany; Heinrich, et al. (2004) *Blood* 104:659-666). Atg5$^{flox}$ mice (Atg5$^{fl/fl}$), with loxP sites flanking exon 3 of Atg5, were provided by Noboru Mizushima (Tokyo Medical and Dental University, Tokyo, Japan; Hara, et al. (2006) *Nature* 441:885-889). All Atg5$^{fl/fl}$ mice analyzed in this study also carried the EpoR-Cre allele. All mice were backcrossed onto the C57BL/6J background (The Jackson Laboratory, Bar Harbor, Me.) for five to seven generations. Experiments were conducted with mice aged 6-24 weeks, with wild-type littermates used as controls. Fetal liver transplants were performed as described previously (Gudmundsson, et al. (2012) *Meth. Mol. Biol.* 879: 123-133). Briefly, 8-week-old C57BL/6 CD45.1 recipient mice were lethally irradiated, then, after a 24-hour interval, they received a transplant of 2×10$^6$ fetal liver cells from CD45.2 day 14.5 embryo donors via tail-vein injection. Engraftment was determined by flow cytometry for CD45 alleles at 4 and 12 weeks after transplant.

Hematologic Analysis.

Mice were analyzed at 1-6 months of age. Blood was collected by submandibular bleeding, anticoagulated with EDTA, and analyzed on a FORCYTE Veterinary Hematology Analyzer. Reticulocytes were quantified with thiazole orange (BD Biosciences) in accordance with the manufacturer's protocol, using an LSR/Fortessa cell analyzer (BD Biosciences), and cell counts were analyzed using FlowJo 10.4.1 software (FlowJo, LLC).

Detection of Globin Precipitates in Erythroid Cells.

Globin precipitates from erythrocytes were analyzed as described (Khandros, et al. (2012) *Blood* 119:5265-5275; Kong, et al. (2004) *J. Clin. Invest.* 114:1457-1466; Alter (1981) *Prog. Clin. Biol. Res.* 60:157-175; Yu, et al. (2007) *J. Clin. Invest.* 117:1856-1865; Sorensen, et al. (1990) *Blood* 75:1333-1336). Briefly, 20 µL of washed RBCs (normalized based on the hematocrit percentage) were lysed and centrifuged at 16,000×g at 4° C. for 30 minutes. The pellets were washed extensively in ice-cold 0.05×PBS. Membrane lipids were extracted with 56 mM sodium borate, pH 8.0, containing 0.1% TWEEN-20, at 4° C. Precipitated globins were dissolved in 8M urea, 10% acetic acid, 10% β-mercaptoethanol, and 0.04% pyronin, fractionated by TRITON-acetic acid-urea (TAU) gel electrophoresis, and stained with COOMASSIE brilliant blue. Soluble hemoglobin fractions were analyzed and quantified as loading controls by using AlphaView SA 3.4.0 (ProteinSimple).

Reticulocyte Pulse-Chase Analysis.

Free α-globin turnover was assessed by pulse-labeling reticulocytes with $^{35}$S-labeled amino acids (Khandros, et al. (2012) *Blood* 119:5265-5275). Briefly, reticulocytes were pulse-labeled with $^{35}$S-cysteine and $^{35}$S-methionine for 30 minutes then chased with unlabeled amino acids±proteasome inhibitor (10 µM MG132) and/or lysosome inhibitor (100 µM chloroquine or 0.2 µM bafilomycin A1). Insoluble α-globin was isolated by TAU gel electrophoresis, analyzed by autoradiography, and quantified using AlphaView SA 3.4.0 (ProteinSimple).

Red Blood Cell Survival.

Red blood cell survival was quantified by biotinylation of the entire RBC cohort and monitoring for RBC replacement (Beauchemin, et al. (2004) *J. Biol. Chem.* 279:19471-19480). Briefly, RBCs were labeled in vivo by intravenous injection of 30 mg/kg N-succinimidyl-6-[biotinamido] hexanoate (Thermo Fisher Scientific). The percentage of biotinylated cells from 2-5 µL of peripheral blood obtained from the tail vein was monitored at 3- to 4-day intervals by flow cytometry of biotinylated cells labeled with streptavidin-PE (BD Biosciences, catalog no. 554061) on a LSR/Fortessa cell analyzer (BD Biosciences).

Electron Microscopy.

Samples were fixed in 2.5% glutaraldehyde in 0.1M sodium cacodylate buffer, pH 7.4, and embedded in 2% low-gelling-temperature agarose. The samples were postfixed in 2% osmium tetroxide in 0.1M cacodylate buffer with 0.3% potassium ferrocyanide for 1.5 hours, dehydrated through a graded series of ethanol/propylene oxide solutions, then infiltrated with and embedded in epoxy resin, which was polymerized at 70° C. overnight. Semi-thin (0.5 µm) sections were stained with toluidine blue for light microscope examination. Ultra-thin (80 nm) sections were cut and imaged using an FEI Tecnai 200 Kv FEG Transmission Electron Microscope with an ATM XR41 digital camera.

Areas of electron-dense α-globin inclusions in reticulocytes were quantified by automated image analysis of electron micrographs. TEM images were analyzed with the FIJI software program and the Trainable Weka Segmentation plugin to produce pixel-based segmentations in order to quantify differences in the numbers and areas of intracytoplasmic hemoglobin precipitates in thalassemic and non-thalassemic samples (Schindelin, et al. (2012) Nat. Meth. 9:676-682; Arganda-Carreras, et al. (2017) Bioinformatics 33:2424-2426).

Pathology Analyses.

Bright-field images of hematoxylin and eosin-stained tissues were acquired with a Nikon Eclipse Ni microscope. Morphologic phenotyping of all cohorts was carried out in a blinded manner by a board-certified veterinary pathologist. A semi-quantitative grading method was used to highlight visual differences in the erythropoiesis in each cohort. The bone marrow, spleen, and liver were first analyzed separately using the following grading scale: grade 0: within normal limits; grade 1: minimal; grade 2: mild; grade 3: moderate; grade 4: marked; grade 5: severe. A total grade for erythropoiesis (final grade) was calculated based on the sum of the grades for each of the three tissues. The final grading scale used to quantify the relative amount of erythropoiesis per mouse was as follows: grades 0-3 indicated that erythropoiesis was within what were considered to be the normal limits; grades 4-6 indicated a mild increase; grades 7-9 indicated a moderate increase; grades 10-12 indicated a marked increase; and grades 13-15 indicated a severe increase. No mouse received a grade consistent with a severe increase in erythropoiesis.

Drug Treatment.

Beginning at 3 months of age, mice received daily injections intraperitoneally of rapamycin (sirolimus, 4 mg/kg; Pfizer) or vehicle (sirolimus vehicle) for 30 days, at which point the animals were euthanized. Tail-vein bleeds were performed twice per week for flow cytometry of reticulocytes and/or determination of erythrocyte lifespan. Blood samples obtained by cardiac puncture were submitted for hematologic analysis and detection of globin precipitates and for reticulocyte sorting for TEM. Tissue samples were submitted for pathology analysis.

Erythroid Differentiation and Treatment of Human $CD34^+$ Cells.

Human $CD34^+$ cells were obtained from de-identified β-thalassemia samples (bone marrow purified from five patients with transfusion dependent β-thalassemia and peripheral blood purified from five patients with non-transfusion dependent β-thalassemia) and from seven healthy donors (protocol number: NCT00669305). $CD34^+$ HSPCs were cultured according to a three-phase erythroid differentiation protocol (Traxler, et al. (2016) Nat. Med. 22:987-990). Erythroid differentiation and maturation were monitored by flow cytometry with an LSR/Fortessa cell analyzer (BD Biosciences), using the following antibodies: anti-CD235a (BD Biosciences), anti-Band3, and anti-α4-integrin (Miltenyi). At the beginning of phase 3 (day 13), cells were treated with rapamycin (10 µM or 20 µM; LC laboratories) or MG132 (1 µM or 2.5 µM; Enzo Life Sciences) for 48 hours.

Hemoglobin Fractionation.

Cells were lysed in Hemolysate reagent (Helena Laboratories, Beaumont, Tex.) and centrifuged. Analysis of globin chains in the supernatant was performed by ion exchange (IE) and reverse phase (RP)-HPLC (Prominence UFLC, Shimadzu). Proteins eluting from the column were quantified by light absorbance at 220, 280, and 415 nm with a diode array detector. The relative amount of free α-globin was calculated from the area of the peak for each condition at 415 nm and normalized based on the DMSO control. The percentage was calculated as follows: % α-globin=[α-chain/ρ-chain (β+γ+δ)×100].

Western Blot Analysis.

Sorted reticulocytes (stained with thiazole orange$^+$ (BD Biosciences) were homogenized in RIPA buffer with protease inhibitor cocktail (Sigma-Aldrich) at 4° C. Large cellular debris was concentrated by centrifugation (1000×g for 5 minutes at 4° C.) and discarded, after which protein was quantified with a PIERCE BCA kit (Thermo Fisher Scientific). Twenty micrograms of each sample were resolved by 12% SDS-PAGE, transferred to a PVDF membrane, using the following antibodies: anti-LC3A/B (CST), anti-P62 (CST), anti-ULK1 (CST) and anti-β-Actin (Sigma Aldrich). Immunoreactive bands were labeled with appropriate secondary antibodies coupled to horseradish peroxidase (Jackson ImmunoResearch Laboratories) then detected with PIERCE ECL Plus Western Blotting Substrate (Thermo Fisher Scientific). The apparent molecular mass of each protein was estimated by comparison to the PAGERULER PRECISION PLUS PROTEIN Ladder (BioRad). Signals were quantified using AlphaView SA 3.4.0 (ProteinSimple). Membranes were treated with Restore PLUS Western Blot Stripping Solution (Thermo Fisher Scientific) to enable the sequential analysis of different proteins on the same membrane.

Statistics.

Statistical analyses were performed using GraphPad Prism 6.0 software. For multiple comparisons, a one-way ANOVA with pairwise comparisons was used. A two-tailed Student's t-test was used for individual comparisons if they were normally distributed.

Example 2: Genetic Ablation of ULK1 in β-Thalassemia Mice $Hbb^{Th3/+}$ mice were crossed with the $Ulk1^{-/-}$ mice and evaluated for 6 months. The results of this analysis indicated that the lifespan of $Ulk1^{-/-}Hbb^{Th3/+}$ mice was significantly shorter than that of $Hbb^{Th3/+}$ mice. Specifically, only 15% of $Hbb^{Th3/+}Ulk1^{-/-}$ mice survived for 30 days, compared to 80% of $Hbb^{Th3/+}Ulk1^{+/+}$ mice (P<0.01). To examine the hematopoietic cell-intrinsic consequences of ULK1 loss in β-thalassemia, embryonic day 14.5 fetal liver cells from $Hbb^{Th3/+}Ulk1^{-/-}$ and control strains (CD45.2) were transplanted into lethally irradiated wild-type CD45.1 hosts. Donor hematopoietic cell engraftment exceeded 92% after 90 days. Loss of Ulk1 exacerbated β-thalassemia, with a 20% reduction in the RBC count (P<0.0001), and a 2-fold increase in the reticulocyte count (P<0.0001) to maintain the same level of blood hemoglobin (Table 1).

TABLE 1

| | Hbb Genotype | | | |
| --- | --- | --- | --- | --- |
| | $Hbb^{+/+}$ | | $Hbb^{Th3/+}$ | |
| | Ulk1 Genotype | | | |
| | $Ulk1^{+/+}$ | $Ulk1^{-/-}$ | $Ulk1^{+/+}$ | $Ulk1^{-/-}$ |
| No. of mice analyzed | 22 | 6 | 29 | 25 |
| RBC (×10$^6$/µL) | 9.29 ± 0.57 | 9.11 ± 0.41 | 7.58 ± 0.68 | 6.13 ± 0.59* |
| Reticulocytes (%) | 3.10 ± 0.51 | 4.01 ± 0.77 | 18.52 ± 3.14 | 32.34 ± 5.53* |

TABLE 1-continued

| | Hbb Genotype | | | |
|---|---|---|---|---|
| | Hbb$^{+/+}$ | | Hbb$^{Th3/+}$ | |
| | Ulk1 Genotype | | | |
| | Ulk1$^{+/+}$ | Ulk1$^{-/-}$ | Ulk1$^{+/+}$ | Ulk1$^{-/-}$ |
| Hb (g/dL) | 13.37 ± 1.11 | 13.77 ± 0.42 | 10.68 ± 0.79 | 10.53 ± 0.84$^{ns}$ |
| Hct (%) | 38.44 ± 3.12 | 41.95 ± 1.88 | 27.69 ± 2.58 | 27.50 ± 2.27$^{ns}$ |
| MCV (fL) | 41.35 ± 1.92 | 46.02 ± 1.02 | 36.51 ± 1.17 | 44.98 ± 2.25* |
| MCH (pg) | 14.39 ± 0.78 | 15.13 ± 0.75 | 14.17 ± 1.40 | 17.36 ± 2.42* |
| MCHC (g/dL) | 34.81 ± 1.69 | 32.88 ± 2.00 | 38.85 ± 4.10 | 38.50 ± 4.11$^{ns}$ |
| RDW (%) | 15.25 ± 1.38 | 16.25 ± 0.92 | 36.03 ± 3.30 | 36.56 ± 3.20$^{ns}$ |

All mice were background-matched and were analyzed at 3 months of age.
RBC, red blood cells;
Hb, hemoglobin;
Hct, hematocrit;
MCV, mean corpuscular volume;
MCH, mean corpuscular hemoglobin;
MCHC, mean corpuscular hemoglobin concentration;
RDW, red cell distribution width.
Data are shown as mean values ± SD.
Hbb$^{Th3/+}$Ulk1$^{+/+}$ vs. Hbb$^{Th3/+}$Ulk1$^{-/-}$ (Student's t-test):
*P < 0.001;
ns: not significant.

Biotin labeling experiments showed that loss of Ulk1 reduced the half-life of circulating RBCs from 7.5 days (for Hbb$^{Th3/+}$Ulk1$^{+/+}$ RBCs) to 5.4 days (for Hbb$^{Th3/+}$Ulk1$^{-/-}$ RBCs) (P<0.0001), as compared to 17.5 days for wild-type (Hbb$^{+/+}$Ulk1$^{+/+}$) RBCs. Phenotypic analysis of these mice at three months of age indicated an increase in splenomegaly in Ulk1$^{-/-}$Hbb$^{Th3/+}$ mice compared to Hbb$^{Th3/+}$ animals as well as increased bone marrow erythroid precursor hyperplasia, and extramedullary erythropoiesis in spleen and liver (Table 2). Of note, there was no significant difference in body weight amongst wild-type, Hbb$^{Th3/+}$, and Ulk1$^{-/-}$Hbb$^{Th3/+}$ mice. Together, these findings show that ULK1 deficiency exacerbates ineffective erythropoiesis and reduces the viability of mature RBCs.

TABLE 2

| | Hbb Genotype | | | |
|---|---|---|---|---|
| | Hbb$^{+/+}$ | | Hbb$^{Th3/+}$ | |
| | Ulk1 Genotype | | | |
| | Ulk1$^{+/+}$ | Ulk1$^{-/-}$ | Ulk1$^{+/+}$ | Ulk1$^{-/-}$ |
| No. of mice analyzed | 22 | 4 | 14 | 11 |
| Bone marrow | 0.27 ± 0.70 | 0.00 ± 0.00 | 3.35 ± 0.63 | 3.87 ± 0.40* |
| Spleen | 0.00 ± 0.00 | 0.00 ± 0.00 | 2.00 ± 0.00 | 3.75 ± 0.52** |
| Liver | 1.09 ± 0.42 | 1.00 ± 0.00 | 1.36 ± 0.50 | 1.81 ± 0.60* |
| Final grade | 1.366 ± 0.90 | 1.00 ± 0.00 | 7.12 ± 0.62 | 9.18 ± 1.32** |

Erythroid precursor accumulation ("red pulp") was quantified by visual inspection of H&E-stained tissue sections from mice with the indicated genotypes. Erythropoiesis was graded on a 6-point scale, with 0 being minimal and 5 representing the highest level. The final grade represents the sum of the grades for each of the three tissues.
Data are shown as mean values ± SDs.
Hbb$^{Th3/+}$Ulk1$^{+/+}$ vs. Hbb$^{Th3/+}$Ulk1$^{-/-}$ mice (Student's t-test):
**P < 0.001;
*P > 0.05.

To investigate whether the loss of ULK1-dependent autophagy caused increased accumulation of precipitated α-globin, circulating RBCs were lysed and the contents were fractionated by centrifugation followed by TRITON-acetic acid-urea (TAU) gel electrophoresis to resolve the α- and β-globin proteins (Khandros, et al. (2012) *Blood* 119: 5265-5275). This analysis indicated that Hbb$^{Th3/+}$ RBCs contained insoluble α-globin, which was increased approximately 2-fold by the loss of ULK1 (P<0.001; FIG. 1).

Transmission electron microscopy (TEM) revealed collections of electron-dense material, presumably α-globin precipitates, in flow cytometry-purified reticulocytes from β-thalassemic mice, but not in those from control mice. Automated image analysis of 100 to 200 cells from multiple mice demonstrated an approximately 2-fold increased area of electron-dense material in Hbb$^{Th3/+}$Ulk1$^{-/-}$ reticulocytes as compared to Hbb$^{Th3/+}$ Ulk1$^{+/+}$ reticulocytes (P<0.05). Moreover, the levels of the autophagy adaptor protein P62 and lipidated forms of the autophagosomal marker protein LC3 were increased in reticulocytes of Hbb$^{Th3/+}$ mice, as compared to wild-type (Hbb$^{47+}$Ulk1$^{+/+}$) reticulocytes, and were even higher in Hbb$^{Th3/+}$Ulk1$^{-/-}$ mice. Thus, the loss of ULK1 increases the accumulation of insoluble α-globin and autophagic compartments in β-thalassemia.

ATG5 is required for most autophagy processes. However, mitochondria are eliminated from reticulocytes in an ATG5-independent, ULK1-dependent form of autophagy (Kundu, et al. (2008) *Blood* 112:1493-1502; Tain, et al. (2009) *Nat. Neurosci.* 12:1129-1135; Honda, et al. (2014) *Nat. Commun.* 5:4004). Therefore, the role of ATG5 in eliminating free α-globin was investigated. Into Hbb$^{Th3/+}$ β-thalassemic mice was introduced a conditional Atg5 allele, in which exon 3 is flanked by loxP sites (Hara, et al. (2006) *Nature* 441:885-889), and a Cre recombinase transgene (EpoR-Cre) that is expressed exclusively in erythroid precursors (Heinrich, et al. (2004) *Blood* 104:659-666). Double-mutant (Hbb$^{Th3/+}$Atg5$^{fl/fl}$) mice were born at a normal Mendelian ratio. At age 4-6 months, Atg5 transcripts and protein levels were reduced by 90% to 95% in Ter119$^+$ bone marrow erythroid precursors. The erythroid indices of Hbb$^{Th3/+}$Atg5$^{fl/fl}$ mice were mildly worsened compared to those of Hbb$^{Th3/+}$ mice, as reflected by 10% reductions in the RBC counts (P<0.001) and 20% increases in the reticulocyte counts (P<0.05) (Table 3).

TABLE 3

| | Hbb Genotype | | | |
|---|---|---|---|---|
| | Hbb$^{+/+}$ | | Hbb$^{Th3/+}$ | |
| | Atg5 Genotype | | | |
| | Atg5$^{fl/+}$ | Atg5$^{fl/fl}$ | Atg5$^{fl/+}$ | Atg5$^{fl/fl}$ |
| No. of mice analyzed | 10 | 10 | 10 | 10 |
| RBC (×10$^6$/μL) | 9.43 ± 0.39 | 9.27 ± 0.43 | 7.60 ± 0.38 | 6.92 ± 0.53** |
| Reticulocytes (%) | 3.31 ± 0.82 | 3.57 ± 0.68 | 20.62 ± 3.91 | 23.95 ± 4.26* |
| Hb (g/dL) | 15.23 ± 0.66 | 14.90 ± 0.68 | 10.85 ± 0.56 | 10.38 ± 0.17* |
| Hct (%) | 42.22 ± 1.67 | 41.54 ± 2.19 | 29.95 ± 1.71 | 28.04 ± 1.01** |
| MCV (fL) | 44.78 ± 0.75 | 44.83 ± 1.47 | 39.44 ± 1.87 | 41.49 ± 2.04* |
| MCH (pg) | 16.17 ± 0.68 | 16.09 ± 0.40 | 14.30 ± 0.88 | 15.38 ± 0.96* |
| MCHC (g/dL) | 36.09 ± 1.47 | 35.89 ± 1.22 | 36.26 ± 1.58 | 37.14 ± 1.46$^{ns}$ |
| RDW (%) | 17.81 ± 0.72 | 18.77 ± 0.82* | 32.62 ± 2.72 | 34.32 ± 2.48$^{ns}$ |

Background-matched male mice were analyzed at 4-6 months of age. All mice carried the EpoR-Cre allele.
Data are shown as mean values ± SDs.
Hbb$^{Th3/+}$Atg5$^{fl/+}$ vs. Hbb$^{Th3/+}$Atg5$^{fl/fl}$ (Student's t-test):
**P < 0.01;
*P < 0.05;
ns: not significant.

ATG5 deficiency in Hbb$^{Th3/+}$ mice had minimal effect on spleen weight. Consistent with the expected impairment in autophagy, the levels of the autophagy adaptor protein P62 were increased in RBC insoluble fractions of Atg5$^{fl/fl}$ and Hbb$^{Th3/+}$Atg5$^{fl/fl}$ mice. However, ATG5 deficiency in Hbb$^{Th3/+}$ mice had minimal effects on the levels of insoluble α-globin. Thus, ATG5 mediates some autophagy processes during erythropoiesis, but is not required for the elimination of free α-globin.

It has been previously demonstrated that the ubiquitin-proteasome system and autophagy degrade excess α-globin in β-thalassemic erythroid cells (Khandros, et al. (2012) *Blood* 119:5265-5275). Systemic administration of the proteasome inhibitor bortezomib to Hbb$^{Th3/+}$ mice induced both autophagy and heat-shock proteins with no net increase in insoluble α-globin (Khandros, et al. (2012) *Blood* 119:5265-5275), suggesting that there is cross-compensation by the protein quality control systems. To investigate how the depletion of ULK1 or ATG5 affects the turnover of insoluble α-globin in β-thalassemia, mutant reticulocytes were pulse-labeled with $^{35}$S-labeled amino acids, chased for various times with unlabeled amino acids with or without various inhibitors, and the soluble and insoluble nascent radiolabeled α-globin in cell lysates was quantified. After 6 hours, Hbb$^{Th3/+}$ reticulocytes had cleared approximately 60% of the labeled insoluble α-globin through mechanisms that were sensitive to proteasome inhibition with MG132 or to late stage autophagy inhibition by chloroquine, or bafilomycin A1. In contrast, autophagy-dependent clearance of insoluble α-globin was fully eliminated in Hbb$^{Th3/+}$Ulk1$^{-/-}$ reticulocytes but was maintained in Hbb$^{Th3/+}$Atg5$^{fl/fl}$ reticulocytes. Thus, in β-thalassemia, insoluble free α-globin is cleared by autophagy that is ULK1-dependent and ATG5-independent.

Example 3: Treatment of a Mouse Model of β-Thalassemia with mTOR Inhibitor

The mechanistic target of rapamycin complex 1 (mTORC1) inhibits autophagy by phosphorylating ULK1 (Laplante & Sabatini (2012) *Cell* 149:274-293; Ganley, et al. (2009) *J. Biol. Chem.* 284:12297-12305; Hosokawa, et al. (2009) *Mol. Biol. Cell* 20:1981-1991; Kim, et al. (2011) *Nat. Cell Biol.* 13:132-141). Therefore, it was determined whether mTORC1 inhibition could ameliorate β-thalassemia by stimulating autophagic clearance of free α-globin. Rapamycin (4 mg/kg) was administered intraperitoneally to β-thalassemic and control mice daily for 30 days, followed by necropsy. In vivo drug activity in reticulocytes was confirmed by reduced phosphorylation of the mTORC1 target ribosomal protein S6 (P<0.001). β-Thalassemic mice treated with rapamycin exhibited numerous indications of reduced RBC pathology, including a 27% increase in RBC count (P<0.001), a 10% increase in Hb (P<0.05), a 44% decrease in reticulocyte count (P<0.001), and an increase in the half-life of circulating RBCs from 6.9 to 12.2 days (P<0.0001; the normal half-life is 18 days) (Table 4).

TABLE 4

| Hbb genotype | Hbb$^{+/+}$ | | Hbb$^{Th3/+}$ | | Hbb$^{Th3/+}$ | |
| --- | --- | --- | --- | --- | --- | --- |
| Ulk1 genotype | Ulk1$^{+/+}$ | Ulk1$^{+/+}$ | Ulk1$^{+/+}$ | Ulk1$^{+/+}$ | Ulk1$^{-/-}$ | Ulk1$^{-/-}$ |
| Treatment | Veh | Rap | Veh | Rap | Veh | Rap |
| No. of mice analyzed | 9 | 9 | 12 | 12 | 9 | 9 |
| RBC (×10$^6$/μL) | 9.22 ± 0.94 | 9.57 ± 1.25$^{ns}$ | 7.51 ± 1.07 | 9.10 ± 1.37*** | 5.20 ± 0.71 | 5.81 ± 0.99$^{ns}$ |
| Reticulocytes (%) | 2.89 ± 0.53 | 2.90 ± 1.21$^{ns}$ | 22.92 ± 3.21 | 13.06 ± 6.67*** | 33.52 ± 5.93 | 34.35 ± 2.78$^{ns}$ |
| Hb (g/dL) | 13.54 ± 1.74 | 13.78 ± 1.99$^{ns}$ | 9.42 ± 0.65 | 10.33 ± 1.07* | 8.45 ± 1.22 | 8.74 ± 1.80$^{ns}$ |
| Hct (%) | 38.74 ± 3.13 | 40.98 ± 5.75$^{ns}$ | 26.44 ± 3.18 | 29.42 ± 3.59* | 23.73 ± 4.59 | 25.42 ± 4.59$^{ns}$ |
| MCV (fL) | 43.31 ± 1.40 | 42.89 ± 1.61$^{ns}$ | 36.99 ± 1.41 | 32.67 ± 3.02*** | 45.58 ± 1.65 | 43.03 ± 1.62** |
| MCH (pg) | 14.54 ± 0.77 | 14.53 ± 0.53$^{ns}$ | 13.37 ± 1.06 | 11.56 ± 1.21*** | 16.30 ± 1.57 | 15.08 ± 1.31$^{ns}$ |
| MCHC (g/dL) | 33.86 ± 1.57 | 33.66 ± 0.76$^{ns}$ | 36.72 ± 1.52 | 35.54 ± 1.01* | 35.67 ± 2.46 | 34.99 ± 2.14$^{ns}$ |
| RDW (%) | 14.10 ± 1.58$^{ns}$ | 14.40 ± 0.91$^{ns}$ | 35.23 ± 3.22 | 31.05 ± 5.23* | 38.22 ± 1.23 | 39.73 ± 0.66$^{ns}$ |

Background-matched 2-month-old mice were treated for 30 days with rapamycin (Rap) or vehicle (Veh) then analyzed. Data are shown as mean values ± SDs. Rapamycin vs. vehicle for all genotypes (Student's t-test):
*P < 0.05;
**P < 0.01;
***P < 0.005;
$^{ns}$not significant.

Rapamycin-treated Hbb$^{Th3/+}$ mice also showed signs of diminished ineffective erythropoiesis, including a reduction in spleen weight (P<0.01), as well as reduced levels of bone marrow erythroid hyperplasia and extramedullary erythropoiesis in the spleen and liver (Table 5). Importantly, rapamycin had no effect on RBC indices or erythropoiesis in wild-type or Hbb$^{Th3/+}$Ulk1$^{-/-}$ mice.

TABLE 5

| Hbb genotype | Hbb$^{+/+}$ | | Hbb$^{Th3/+}$ | | Hbb$^{Th3/+}$ | |
| --- | --- | --- | --- | --- | --- | --- |
| Ulk1 genotype | Ulk1$^{+/+}$ | Ulk1$^{+/+}$ | Ulk1$^{+/+}$ | Ulk1$^{+/+}$ | Ulk1$^{-/-}$ | Ulk1$^{-/-}$ |
| Treatment | Veh | Rap | Veh | Rap | Veh | Rap |
| No. of mice analyzed | 9 | 9 | 9 | 9 | 8 | 10 |
| Bone marrow | 0.00 ± 0.00 | 0.00 ± 0.00$^{ns}$ | 2.55 ± 1.01 | 1.75 ± 1.67$^{ns}$ | 3.00 ± 0.53 | 3.30 ± 0.48$^{ns}$ |
| Spleen | 0.00 ± 0.00 | 0.00 ± 0.00$^{ns}$ | 3.00 ± 0.00 | 2.37 ± 0.52** | 2.88 ± 0.35 | 3.20 ± 0.79$^{ns}$ |
| Liver | 0.22 ± 0.44 | 0.44 ± 0.53$^{ns}$ | 1.22 ± 0.44 | 0.87 ± 0.35$^{ns}$ | 1.78 ± 0.44 | 1.10 ± 0.31** |
| Final grade | 0.22 ± 0.44 | 0.44 ± 0.53$^{ns}$ | 6.78 ± 0.83 | 5.00 ± 1.85* | 7.75 ± 0.88 | 7.60 ± 1.07$^{ns}$ |

Figure 2:
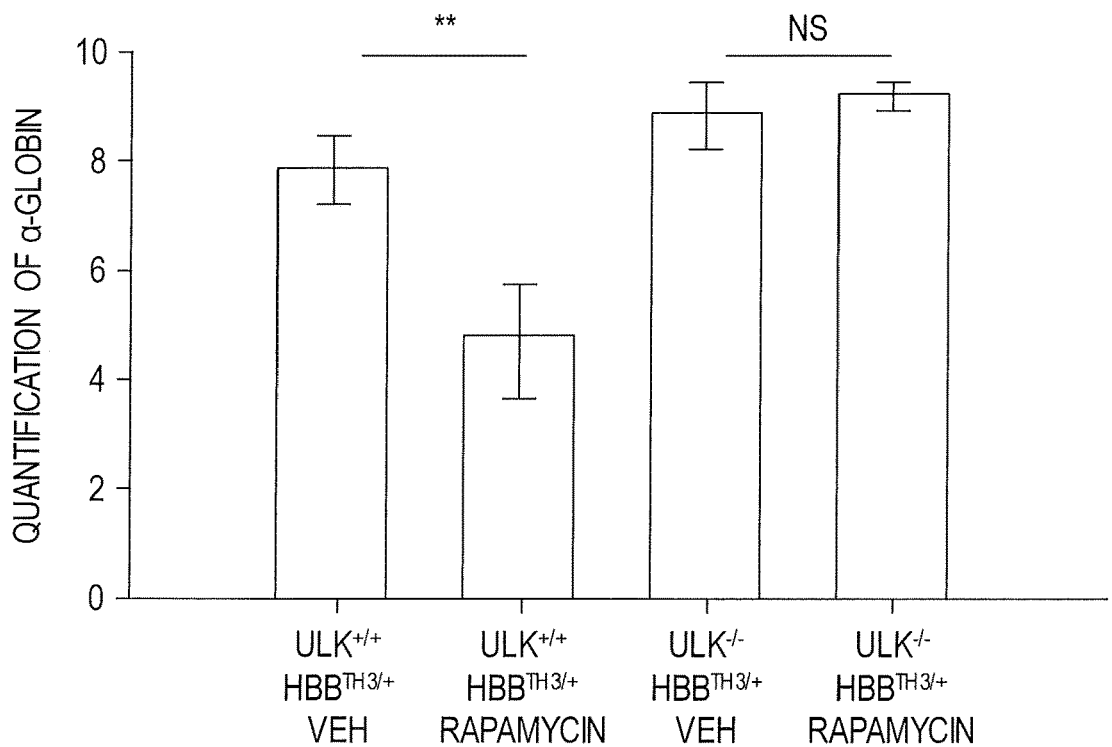
FIG. 2 shows the decrease of insoluble $\alpha$-globin chains of Hbb$^{Th3/+}$ mice treated with rapamycin compared to vehicle (Veh) controls and no modification observed of Ulk1$^{-/-}$ Hbb$^{Th3/+}$ mice. Hbb$^{Th3/+}$+Veh, n=7; Hbb$^{Th3/+}$+Rap, n=7; Hbb$^{Th3/+}$Ulk1$^{-/-}$+Veh, n=7; Hbb$^{Th3/+}$Ulk1$^{-/-}$+Rap, n=7. Results are presented as mean±SD; **P<0.01; n.s., not significant.

RBCs and their precursors were studied to investigate the mechanisms by which rapamycin ameliorates the effects of β-thalassemia. Insoluble α-globin in reticulocytes from rapamycin-treated Hbb$^{Th3/+}$ mice was decreased by approximately 50% (FIG. 2). Consistent with these findings, TEM showed an approximately 60% reduction in electron-dense aggregates in reticulocytes from β-thalassemic mice treated with rapamycin, as compared to those from vehicle-treated controls (P<0.0001). The levels of autophagosomal membrane-bound LC3-II decreased in reticulocytes of Hbb$^{Th3/+}$ mice treated with rapamycin, suggesting enhanced flux through the autophagy pathway in these animals. In contrast, rapamycin had no effect on the accumulation of insoluble α-globin in Hbb$^{Th3/+}$Ulk1$^{-/-}$ mice (FIG. 2). Together, these studies demonstrate that rapamycin treatment of β-thalassemic mice stimulates ULK1-dependent autophagy to reduce free α-globin precipitates, alleviate ineffective erythropoiesis, and extend RBC lifespan.

To investigate the therapeutic potential of rapamycin in human β-thalassemia, rapamycin was applied to erythroid precursors generated by in vitro differentiation of CD34$^{+}$ hematopoietic stem and progenitor cells (HSPCs) from patients with β-thalassemia who require regular RBC transfusions (transfusion-dependent; n=5) and from those with variable degrees of anemia who require transfusions intermittently or not at all (non-transfusion-dependent; n=5) (Table 6 and Table 7).

TABLE 6

| | β-Thalassemia | Reference range | |
|---|---|---|---|
| | NTD | Low | High |
| Number analyzed | 5 | | |
| RBC (×10$^6$/μL) | 4.96 ± 0.9 | 4.0 | 5.2 |
| Hb (g/dL) | 9.9 ± 1.4 | 12.0 | 16.0 |
| Hct (%) | 30.04 ± 5.4 | 36.0 | 46.0 |
| MCV (fL) | 60.9 ± 6.1 | 80.0 | 100.0 |
| MCH (pg) | 20.3 ± 1.2 | 26.0 | 34.0 |
| MCHC (g/dL) | 33.2 ± 1.8 | 31.0 | 37.0 |
| RDW (%) | 23.4 ± 1.6 | 11.4 | 14.9 |

NTD, non-transfusion dependent.
CBCs for patients with transfusion-dependent β-thalassemia were omitted because of the contribution of the transfused blood.
Data are shown as mean values ± SD.

TABLE 7

| Transfusion-dependent (TD) β-thalassemia | | |
|---|---|---|
| Simplified genotypes | HBB (β-globin) | HBA1/HBA2 (α-globin) |
| β$^+$/β$^0$; αα/αα | IVS-I-6; p.39Gln* | αα; αα |
| β$^0$/wt; αα/αα | IVS-I-1; wt | αα; αα |
| β$^+$/β$^0$; αα/αα | IVS-I-110; p.39Gln* | αα; αα |

| Non-transfusion-dependent (NTD) β-thalassemia | | |
|---|---|---|
| Simplified genotypes | HBB | Alpha Gene |
| β$^+$/β$^{++}$; αα/αα | IVS-I-110/IVS-II-844 | αα; αα |
| β$^0$/β$^0$; -α$^{3.7}$/-α$^{3.7}$ | p.39Gln*/cod6 | α$^{-3.7}$; α$^{-3.7}$ |
| β$^0$/wt; ααα/αα | p.39Gln*/wt | ααα; αα |

Patient or control CD34$^{+}$ cells were purified from either peripheral blood (for control and NTD β-thalassemia cells) or bone marrow (for TD β-thalassemia cells) and grown in culture under conditions that support erythroid differentiation (Traxler, et al. (2016) Nat. Med. 22:987-990). β-Thalassemia erythroblasts exhibited accelerated maturation, as indicated by the earlier appearance of the late-stage erythroid marker Band3 and the loss of the integrin subunit CD49d. Reverse-phase high-performance liquid chromatography (RP-HPLC) analysis of hemogiobinized erythroblasts generated from patients with TD or NTD β-thalassemia revealed α-chain excesses (α-chain/β-like chain[β+γ+δ]) of approximately 40% and 15%, respectively. Non-denaturing ion-exchange (IE) HPLC identified a free α-globin peak in TD and NTD β-thalassemic erythroblasts, but not in control cells. Rapamycin (10 μM or 20 μM) or the proteasome inhibitor MG132 was added to day 13 cultures, which contained mid- to late-stage erythroblasts, and α-globin accumulation was determined by HPLC two days later. As expected, proteasome inhibition by MG132 raised free α-globin levels in β-thalassemic erythroblasts and also induced cell death. In contrast, rapamycin treatment reduced free α-globin by 40% and 85% in TD β-thalassemia (P<0.0001) and NTD β-thalassemic erythroblasts (P<0.001), respectively, with no deleterious effect on cell survival. Previous studies indicated that rapamycin could elevate fetal hemoglobin level in cultures of erythroblasts derived from human CD34$^{+}$ cells (Fibach, et al. (2006) Eur. J. Haematol. 77:437-441; Pecoraro, et al. (2015) Hemoglobin 39:225-229), even if this effect was not observed in the present studies. Thus, rapamycin reduces the accumulation of free α-globin in primary erythroid cells derived from patients with β-thalassemia, most likely by inhibiting mTORC1, with consequent derepression of ULK1-mediated autophagy.

What is claimed is:

1. A method for removing excess free α-globin in reticulocytes or erythrocytes comprising contacting reticulocytes or erythrocytes with an effective amount of an agonist that directly activates Unc-51 Like autophagy activating Kinase (ULK), AMP-Activated Protein Kinase (AMPK), or Glycogen synthase kinase 3 (GSK3) thereby removing excess free α-globin in the reticulocytes or erythrocytes.

2. A method for removing excess free, insoluble α-globin in reticulocytes or erythrocytes comprising contacting reticulocytes or erythrocytes with an effective amount of an agent that activates Unc-51 Like autophagy activating Kinase (ULK) thereby removing excess free, insoluble α-globin in the reticulocytes or erythrocytes, wherein the agent inhibits Mechanistic Target Of Rapamycin (mTOR).

3. A method for treating a thalassemia comprising administering to a subject in need thereof an effective amount of an agonist that directly activates Unc-51 Like autophagy activating Kinase (ULK), AMP-Activated Protein Kinase (AMPK), or Glycogen synthase kinase 3 (GSK3) and stimulates ULK1-dependent autophagy thereby treating the subject's thalassemia.

4. A method for treating a thalassemia comprising administering to a subject in need thereof an effective amount of an agent that activates Unc-51 Like autophagy activating Kinase (ULK), wherein the agent inhibits Mechanistic Target Of Rapamycin (mTOR) and is not an ATP-competitive mTOR kinase inhibitor.

5. The method of claim 3, wherein the thalassemia is β-thalassemia.

6. The method of claim 4, wherein the thalassemia is β-thalassemia.

7. The method of claim 2, wherein the agent that inhibits mTOR is not an ATP-competitive mTOR kinase inhibitor.

* * * * *